(12) United States Patent
Brothers

(10) Patent No.: US 7,999,146 B2
(45) Date of Patent: Aug. 16, 2011

(54) DRESSING AND METHOD OF TREATMENT FOR A WOUND

(75) Inventor: Lisa M. Brothers, Ingleside, IL (US)

(73) Assignee: Zymurgy LLC

( * ) Notice: Subject to any disclaimer, the term of this patent is extended or adjusted under 35 U.S.C. 154(b) by 736 days.

(21) Appl. No.: 11/195,360

(22) Filed: Aug. 1, 2005

(65) Prior Publication Data

US 2006/0029651 A1   Feb. 9, 2006

Related U.S. Application Data

(60) Provisional application No. 60/592,983, filed on Jul. 30, 2004.

(51) Int. Cl.
*A61F 13/00* (2006.01)

(52) U.S. Cl. .......................................... 602/54; 424/445

(58) Field of Classification Search ........................ None
See application file for complete search history.

(56) References Cited

U.S. PATENT DOCUMENTS 6,479,725 B1 * 11/2002 Brothers ......................... 602/54

OTHER PUBLICATIONS

T.B. Bruns & J.M. Worthington "Ussing Tissue Adhesive for Wound Repair: A Practical Guide to Dermabond" American Family Physician, 2000, 61(5), pp. 1383-1388.*

W.T. Zempsky et al., "Randomized Controlled Comparison of Cosmetic Outcomes of Simple Facial Lacerations Closed with Steri Strip Skin Closures or Dermabond Tissue Adhesive", Pediatric Emer. Care, 2004, 20(8), pp. 519-524.*

* cited by examiner

*Primary Examiner* — Frederick Krass
*Assistant Examiner* — Brian Gulledge
(74) *Attorney, Agent, or Firm* — Cherskov & Flaynik

(57) ABSTRACT

A dressing and method for treating high-tension wounds. First and second layers of a 2-octyl cyanoacrylate 16 adhesive are applied to a short, high-tension wound, with the first and second layers covering the wound and extending to at least about 2.5 mm (0.0984 in.) from each side of the wound. The first layer is allowed to set and polymerize before the second layer of 2-octyl cyanoacrylate is applied. The second layer extends at least about 2.5 mm (0.0984 in.) beyond each edge of the first layer. In the case of a long, high-tension wound, a third layer is applied after the first and second layers are allowed to set and polymerize. The third layer is at least about 2.5 mm (0.0984 in.) wide and is substantially perpendicular to the first and second layers. The third layer may occur intermittently every 2.5 cm (0.984 in.) over the length of the wound, and preferably extends at least about 5 mm (0.197 in.) beyond the edge of the first layer.

11 Claims, 1 Drawing Sheet

DRESSING AND METHOD OF TREATMENT FOR A WOUND

This Utility Patent Application claims the benefits of U.S. Provisional Patent Application No. 60/592,983, filed on Jul. 30, 2004.

TECHNICAL FIELD

This invention relates generally to the treatment of a wound. More particularly, this invention relates to the treatment of a high-tension wound via the application of a 2-octyl cyanoacrylate and like material directly to the wound site.

BACKGROUND OF THE INVENTION

In the medical field, there are several different methods currently known for the treating and closing of wounds resulting from surgical incisions, lacerations, punctures and the like. Devices such as sutures, staples, skin tapes, and adhesives have been used when treating these different types of wounds. However, many of these devices have shortcomings. For example, sutures and surgical staples involve inflicting additional trauma to the wound surface since the needle or staple must pass through the tissue on the edges of the wound. Sutures and staples can also cause increased tension at the site, which will result in increased scarring. Further, when sutures and staples are used, the body treats them as foreign objects. This causes the body to increase its rate of reepithelialization at the wound site. The greater the rate of reepithelialization, the greater amount of scar tissue produced. Finally, sutures or surgical staples often require removal in a second procedure, resulting in additional inconveniences and potential discomfort to the patient.

Surgical strips, on the other hand, are typically used on superficial wounds due to their poor tensile strength. The low holding power of surgical strips causes the strips to prematurely fall off and the wound to open, particularly when in the presence of moisture. All of these examples hold true for wounds occurring in human and veterinary patients.

For these reasons, it has become more common for medical personnel to apply adhesives directly to a wound. For example, 1-butyl cyanoacrylate, commonly sold under the names Indermil™, Histacryl Blue™, Nexabond, and Vetbond™ have been used to aid in the closure of wounds. After the wound has reached homeostasis and the wound edges approximated, these materials are applied directly to the wound, permitting the wound to heal over time without the use of sutures, staples, and skin tapes. However, the use of 1-butyl cyanoacrylate has been thus far fairly limited. Due to the brittleness of the 1-butyl cyanoacrylate, the material has had problems flexing with the movement of the body. This led to the use of 1-butyl cyanoacrylate material in only short, low-tension wounds.

Another type of material that is used in the medical field is 2-octyl cyanoacrylate, which is sold under the commercial name Dermabond™ and Nexaband™. 2-octyl cyanoacrylate is a type of glue that can be used on any area of the body for wounds of varying lengths and sizes. Currently, the recommended and approved technique for applying Dermabond™ to a wound is by applying three identical layers over the top of the wound. U.S. Pat. No. 6,479,725 to Brothers describes a technique for dressing wounds using at least four distinct and separate layers of octyl cyanoacrylate. However, this technique has problems; the tensile strength of the layers is higher than the surrounding skin. This causes dehiscence of the wound at either edge of the dressing, thus creating another wound or wounds needing repair. The patient experiences additional inconveniences and discomfort because the wound has to be treated again. If the dehiscence happens more than 24 hours after an injury, all of the patient's wounds will have to be sutured due to the increased risk of infection.

The present invention improves on current techniques by limiting the layers necessary, and thereby decreasing the tensile strength. By decreasing the tensile strength, a tensile strength is achieved that is closer to skin's own strength and avoids dehiscence. The present invention discloses a new dressing having a much lower tensile strength that is very close to the actual strength of human skin and animal hide. By creating new techniques that utilize fewer layers, less adhesive material is used, resulting in cost savings. Instead of using one vial for every four inches, one vial may be used for 5 to 6 inches 2-octyl cyanoacrylates have also been polymerized for the use of wound closure inside the body. The development of oxyalkene, alkylene carbonate, alkyl ester and alkyl cyanoacrylate, among others, have facilitated this.

The same principles of application techniques are applicable to internal and external use in both humans and animal patients. This opens the doors for many different advances in medical care.

SUMMARY OF THE INVENTION

A dressing and method for treating a high-tension wound comprises the application of three layers of 2-octyl cyanoacrylate to a wound surface. The first, second and third layers are applied with each layer covering the wound or a portion of the wound and extending to at least about 5 mm from each side of the wound. Thirty seconds are allowed between the first and second layers to allow the cyanoacrylate to polymerize. The third layer is applied when the second layer has begun to polymerize. The third layer is applied perpendicular to the first and second layers, and occurs in one-inch intervals over the length of the wound. For high tension wounds that are shorter than one inch, the first two layers can be used by themselves.

It is therefore an object of the invention to provide an improved method for applying an adhesive material to a wound. It is a further object of the invention to provide a method for treating a wound with 2-octyl cyanoacrylate material that reduces or minimizes the amount of scarring around the wound site. It is still another object of the invention to provide a method of applying 2-octyl cyanoacrylate material to a wound that reduces or minimizes dehiscence around the wound. It is yet another object of the present invention to provide a method for applying 2-octyl cyanoacrylate material to a high-tension wound that reduces or minimizes the occurrence of scarring and/or dehiscence around the wound site. Finally, it is another object of the present invention to provide a method of applying 2-octyl cyanoacrylate to a wound, such that an individual will have increased difficulty picking or peeling the material away from the wound.

Briefly, the invention provides a dressing for treating a short, high-tension wound consisting of: a first layer comprising a cyanoacrylate adhesive, the first layer extending beyond each side of the wound; wherein the first layer is polymerized over the wound; and a second layer comprising a cyanoacrylate adhesive, the second layer extending beyond each side of the wound. The first layer extends to at least about 5 mm (0.197 inches) from each side of the wound. The second layer covers at least about 2.5 mm (0.0984 inches) from each side of the wound, and may also extend at least about 2.5 mm beyond each edge of the first layer. The second layer may also extend at least about 2.5 mm (0.0984 inches) beyond each edge of the first layer.

Also provided is a dressing for treating a long, high-tension wound consisting of: a first layer comprising a cyanoacrylate adhesive, the first layer extending beyond each side of the wound; a second layer comprising a cyanoacrylate adhesive, the second layer extending beyond each side of the wound; wherein the first and second layers are polymerized over the wound; and a third layer comprising a cyanoacrylate adhesive, the third layer covering a portion of the first and second layers.

The invention also provides a dressing for treating a short, high-tension wound comprising a first layer comprising 2-octyl cyanoacrylate adhesive, the first layer extending beyond each side of the wound; where in the first layer is polymerized over the wound; and a second layer comprising 2-octyl cyanoacrylate adhesive, the second layer extending beyond each side of the wound.

A dressing for treating a long, high-tension wound is provided, the dressing comprising a first layer comprising 2-octyl cyanoacrylate adhesive, the first layer extending beyond each side of the wound; a second layer comprising 2-octyl cyanoacrylate adhesive, the second layer extending beyond each side of the wound; wherein the first and second layers are polymerized over the wound; and a third layer comprising 2-octyl cyanoacrylate adhesive, the third layer covering a portion of the first and second layers.

The invention also provides a method for treating a short, high-tension wound consisting of the steps of defining and cleaning a high-tension wound; tensioning an area of the high-tension wound; applying a first layer of a cyanoacrylate adhesive directly to the wound and extending the layer beyond each side of the wound; polymerizing the first layer over the wound; and applying a second layer of a cyanoacrylate adhesive directly over the first layer and extending the second layer beyond the wound.

A method for treating a long, high-tension wound is provided consisting of the steps of: defining and cleaning a high-tension wound; tensioning an area of the high-tension wound; applying a first layer of a cyanoacrylate adhesive directly to the wound and extending the layer beyond each side of the wound; polymerizing the first layer over the wound; applying a second layer of a cyanoacrylate adhesive directly over the first layer and extending the second layer beyond the wound; polymerizing the second layer over the wound; and applying a third layer of a cyanoacrylate adhesive, covering a portion of the first and second layers.

The invention also provides a method for treating a short, high-tension wound, comprising the steps of: defining and cleaning a high-tension wound; tensioning an area of the high-tension wound; applying a first layer of a 2-octyl cyanoacrylate adhesive directly to the wound and extending the layer beyond each side of the wound; polymerizing the first layer over the wound; and applying a second layer of a 2-octyl cyanoacrylate adhesive directly over the first layer and extending the second layer beyond the wound.

A method for treating a long, high-tension wound is provided, the method comprising the steps of defining and cleaning a high-tension wound; tensioning an area of the high-tension wound; applying a first layer of a 2-octyl cyanoacrylate adhesive directly to the wound and extending the layer beyond each side of the wound; polymerizing the first layer over the wound; applying a second layer of a 2-octyl cyanoacrylate adhesive directly over the first layer and extending beyond the wound; polymerizing the second layer over the wound; and applying a third layer of a 2-octyl cyanoacrylate adhesive, covering a portion of the first and second layers.

These and other objects, advantages and features of the invention, together with organization and manner of operation thereof, will become apparent from the following detailed description when taken into conjunction with the accompanying drawings, wherein like elements have like numerals throughout the drawings described below.

DETAILED DESCRIPTION

While the present invention is susceptible of an embodiment in many different forms, this disclosure will describe in detail at least one preferred embodiment, and possible alternative embodiments, of the invention with the understanding that the present disclosure is to be considered merely as an exemplification of the principles of the invention and is not intended to limit the broad aspect of the invention to the specific embodiments illustrated.

Figure 1:
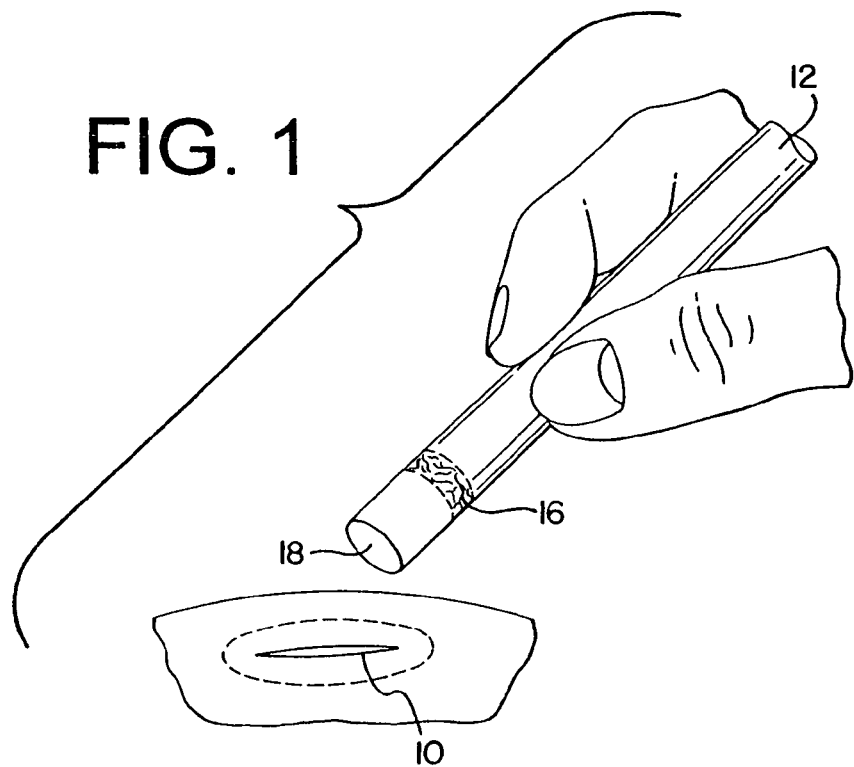
FIG. 1 is an isometric view of one embodiment of the present invention illustrating the application of cyanoacrylate to a wound site.
Figure 2:
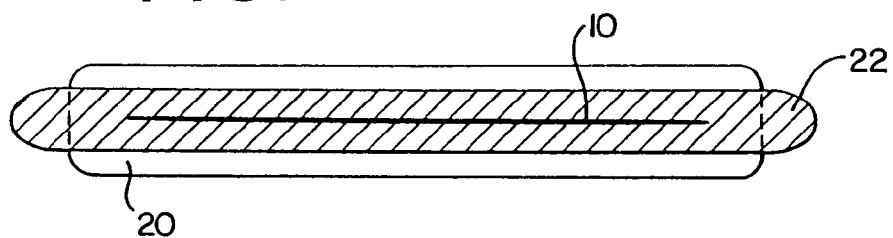
FIG. 2 is a top view of one embodiment of the present invention illustrating a wound after two layers of cyanoacrylate have been applied.
Figure 3:
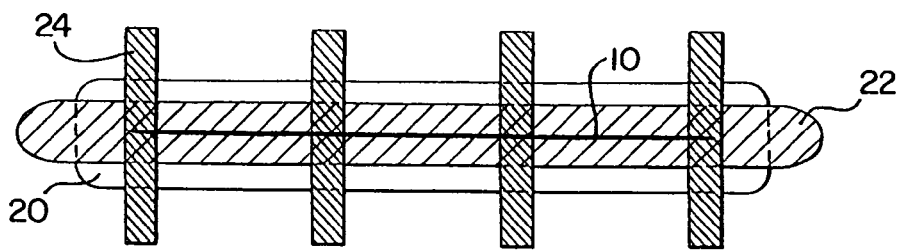
FIG. 3 is a top view of one embodiment of the present invention the wound after three layers of cyanoacrylate have been applied.

According to the present invention, with reference to FIGS. 1-3, the treatment of a wound comprises the use of the adhesive material 2-octyl cyanoacrylate 16. This topical skin adhesive is widely commercially available; for example, the adhesive is sold under the commercial name Dermabond™ and Nexabond™. The adhesive is applied to a wound site 10 through the use of an applicator 12. A vial (not shown) inside the applicator 12 stores the unused 2-octyl cyanoacrylate 16 until application, and the material is applied to the wound site 10 via the applicator tip 18. While in the applicator 12, the unused 2-octyl cyanoacrylate 16 is in liquid form. The material will quickly set after it is applied to the wound site 10.

Under the present invention, 2-octyl cyanoacrylate 16 adhesive can be applied to wounds located both internally and externally on either a human or animal patient. More specifically, this invention is directed to high-tension wounds. The term "wound" is intended to include surgical incisions, lacerations, punctures and cuts, and the like. "High-tension" wound sites are defined as areas at or near a joint, and include areas at or near an elbow or knee. Other high tension areas are mid-sternal chest, post cesarean section wound, and joint replacement surgeries. It is important to provide extra tensile strength to high-tension wounds to prevent a high rate of reepithelialization that causes severe scars. In the case where the wound is located in a high tension area, the joint should preferably be tensioned to at least about a 45-degree angle before applying the adhesive in order to compensate for any stretching of the area that may occur after application.

In one embodiment of the present invention, 2-octyl cyanoacrylate 16 is applied to a wound site 10 as shown in FIGS. 1-3. After the wound site 10 is defined and cleaned, the user squeezes the applicator 12, causing some 2-octyl cyanoacrylate 16 to seep through the applicator tip 18. The user then applies multiple layers of 2-octyl cyanoacrylate 16 to the wound site 10 according to the present invention.

The present invention is directed to both short, high-tension wounds and long, high-tension wounds. A short, high-tension wound is a wound that is about 2.5 cm (0.984 in.) or smaller. A long, high-tension wound is a wound that is greater than about 2.5 cm (0.984 in.). When treating a short, high-tension wound preferably two separate layers, a first layer 20 and a second layer 22 of adhesive material are applied to wound site 10, with none of the layers 20 and 22 extending more than about five millimeters away from the nearest edge of the wound site 10. The second layer 22 is preferably applied to the wound site 10 at least about ten to fifteen seconds after the first layer 20 has been applied, allowing the first layer 20 to properly set and polymerize. For long, high-tension wounds where a third layer 24 is required, the third layer 24 is preferably applied about ten to fifteen seconds after the second layer 22 has been applied, allowing both the first layer 20 and the second layer 22 to properly set and polymerize. Before and while applying the layers 20, 22, and 24 the user may approximate the wound edges with their fingers while wearing latex-free gloves.

In one embodiment, for short, high-tension wounds, the first layer 20 should be applied directly over the wound site 10 extending at least about 5 mm (0.197 in.) from each edge of the wound site 10. After the first layer 20 has properly set and polymerized, the second layer 22 should be applied directly over the wound site 10 extending at least about 2.5 mm (0.0984 in.) beyond both sides of the wound site 10. The second layer 22 should cover a portion of the first layer 20, and the second layer 22 should also extend at least about 2.5 mm (0.0984 in.) beyond the first layer 20 on both ends as shown in FIG. 2. It is important that at least 2.5 mm (0.0984 in.) of the extending edge of the second layer 22 covers the first layer 20. Under this arrangement, the application allows the tension, created by the layers, to be more evenly distributed across the material covering the wound site 10. This placement also aids in more evenly distributing the tension created by 2-octyl cyanoacrylate while increasing the overall strength of the dressing.

Additionally, there are other variations to the method previously described for applying 2-octyl cyanoacrylate to a long, high-tension wound. For example, the first layer 20 should be applied directly over the wound site 10 extending at least about 5 mm (0.197 in.) from each edge of the wound site 10. After the first layer has properly set and polymerized, the second layer 22 should be applied directly over the wound site 10 extending at least about 2.5 mm (0.0984 in.) beyond both sides of the wound site 10. The second layer 22 should cover a portion of the first layer 20. The second layer 22 will also extend at least about 2.5 mm (0.0984 in.) beyond the first layer 20 on both ends. After the second layer 22 has properly set and polymerized, the third layer 24 should be applied so that it covers a portion of the first layer 20, a portion of the second layer 22, and a portion of the wound site 10. The third layer 24 may be a strip that is at least about 5 mm in width. The third layer 24 should be substantially perpendicular to the first and second layers 20 and 22, as well. Where the third layer is multiple strips, as shown in FIG. 3, the strips should occur at least about every 2.5 cm (0.984 in.) over the length of the wound site 10. The third layer 24 will extend beyond each edge of the first layer 20 by at least about 5 mm (0.197 in.). The additional third layer aids in strengthening the entire wound dressing and helps distribute the tension across the dressing. The enlarged surface area created by this application decreases the surface tension on the dressing. Furthermore, by decreasing the surface tension, the rate of reepithelialization is decreased.

While preferred embodiments have been shown and described, it should be understood that changes and modifications can be made therein without departing from the invention in its broader aspects. For example, it is possible that 2-octyl cyanoacrylate could be applied in slightly different locations relative to the wound site, or that different orientations could be used to create an effective dressing. Furthermore, other materials with properties similar to 2-octyl cyanoacrylate, such as a compound selected from the group consisting of oxyalkene, alkylene carbonate, alkyl ester, and alkyl 2-octyl cyanoacrylate, could be used on a wound while still creating an effective wound dressing in accordance with the invention's broader aspects. For example, the solid cyanoacrylate adhesive compositions disclosed in U.S. Pat. No. 6,797,107 B1, incorporated herein by reference, are suitable materials. Those compositions typically include at least one cyanoacrylate monomer having a moiety selected from the group consisting of a C1-16 alkyl, cycloalkyl, alkenyl, alkynl, cylcoalkenyl, alkaryl, aralkyl or aryl group, carboxy alkyl, any of which maybe optionally substituted or interrupted with non-basic groups, such as oxo, halo, silicone and ether oxygen, provided the adhesive qualities are not compromised. For instance the moiety maybe selected from the group consisting of a methyl, ethyl, n-propyl, isopropyl, n-butyl, isobutyl, pentyl, neo-pentyl, hexyl, n-octyl, 2-octyl (as noted supra), allyl, methaallyl, crotyl, propargyl, cyclohexl, benzyl, phenyl, cresyl, 2-chlorobutyl, trifluorethyl, 2-methoxyethyl, 3-methoxybutyl, 2-ethoxyethyl, and 2-propxyethyl.

Various features of the invention are defined in the following claims:

I claim:

1. A method for treating a high-tension wound comprising: defining and cleaning the high-tension wound located at a high-tension wound site; tensioning an area of the high-tension wound; applying a first layer of a cyanoacrylate adhesive directly to the high-tension wound and extending the layer beyond each side of the high-tension wound; polymerizing the first layer over the high-tension wound; and applying a second layer of a cyanoacrylate adhesive directly over the first layer and extending the second layer beyond the high-tension wound, polymerizing the second layer over the high-tension wound and applying a third and final layer of a cyanoacrylate adhesive, wherein said third layer covers a portion of the first and second layers and wherein the step of applying a third layer to extend beyond the wound comprises the step of applying the cyanoacrylate perpendicular to the first and second layers covering a portion of the first and second layers.

2. The method of claim 1, wherein the step of polymerizing comprises the step of delaying the step of applying a second and third layer for a period of 10 to 15 seconds.

3. The method of claim 1, wherein the step of tensioning an area of the wound comprises the step of flexing an affected joint approximately 45° degrees.

4. The method of claim 1, wherein the step of applying a third layer comprises the step of intermittently applying the third layer over the length of the first and second layers.

5. The method of claim 1 wherein the cyanoacrylate contains a moiety selected from the group consisting of a C1-16 alkyl, cycloalkyl, alkenyl, alkynl, cylcoalkenyl, alkaryl, aralkyl or aryl group, carboxy alkyl, any of which maybe optionally substituted or interrupted with non-basic groups.

6. The method of claim 1 wherein the first layer is applied over the wound to extend at least 5 mm from each edge of the wound and the second layer extends at least 2.5 mm beyond the first layer on both ends.

7. The method of claim 1 wherein the first layer is applied over the wound to extend at least 5 mm from each edge of the wound, the second the second layer extends at least 2.5 mm beyond the first layer on both ends, and the third layer comprises one or more strips of 5 mm width applied perpendicular to the first layer and the second layer and extending at least 5 mm beyond the first layer.

8. The method of claim 5 wherein the cyanoacrylate contains a moiety selected from the group consisting of methyl, ethyl, n-propyl, isopropyl, n-butyl, isobutyl, pentyl, neo-pentyl, hexyl, n-octyl, 2-octyl, allyl, methaallyl, crotyl, propargyl, cyclohexl, benzyl, phenyl, cresyl, 2-chlorobutyl, trifluorethyl, 2-methoxyethyl, 3-methoxybutyl, 2-ethoxyethyl, and 2-propxyethyl.

9. The method of claim 1 wherein the adhesive is applied to internal wounds.

10. The method of claim 1 wherein the adhesive is applied to skin surface wounds.

11. The method of claim 5, wherein the non-basic group is an oxo, halo, silicone, or ether oxygen group.

* * * * *